United States Patent
Maker

(10) Patent No.: US 11,732,305 B2
(45) Date of Patent: Aug. 22, 2023

(54) METHOD AND KIT FOR DIAGNOSING EARLY STAGE PANCREATIC CANCER

(71) Applicant: THE BOARD OF TRUSTEES OF THE UNIVERSITY OF ILLINOIS, Urbana, IL (US)

(72) Inventor: Ajay Maker, Evanston, IL (US)

(73) Assignee: The Board of Trustees of the University of Illinois, Urbana, IL (US)

( * ) Notice: Subject to any disclaimer, the term of this patent is extended or adjusted under 35 U.S.C. 154(b) by 234 days.

(21) Appl. No.: 16/499,389

(22) PCT Filed: Mar. 29, 2018

(86) PCT No.: PCT/US2018/025027
§ 371 (c)(1),
(2) Date: Sep. 30, 2019

(87) PCT Pub. No.: WO2018/183603
PCT Pub. Date: Oct. 4, 2018

(65) Prior Publication Data
US 2021/0102255 A1     Apr. 8, 2021

Related U.S. Application Data

(60) Provisional application No. 62/478,860, filed on Mar. 30, 2017.

(51) Int. Cl.
*C12Q 1/6886*     (2018.01)
(52) U.S. Cl.
CPC ...... *C12Q 1/6886* (2013.01); *C12Q 2600/112* (2013.01); *C12Q 2600/158* (2013.01)
(58) Field of Classification Search
CPC ............... C12Q 2600/112; C12Q 2600/158
See application file for complete search history.

(56) References Cited

U.S. PATENT DOCUMENTS

| | | | | |
|---|---|---|---|---|
| 2002/0150894 A1* | 10/2002 | Batra | .................. | C12Q 1/6886 435/6.16 |
| 2005/0170373 A1* | 8/2005 | Monforte | ............ | C12Q 1/6837 435/6.14 |
| 2006/0166230 A1* | 7/2006 | Baker | .................... | G16B 25/10 435/6.14 |
| 2011/0003706 A1 | 1/2011 | Almouzni | | |
| 2014/0134646 A1* | 5/2014 | Martin | ................. | G01N 33/577 435/7.23 |
| 2014/0236166 A1 | 8/2014 | Park | | |
| 2017/0022571 A1 | 1/2017 | Malafa | | |

FOREIGN PATENT DOCUMENTS

| | | | | |
|---|---|---|---|---|
| WO | WO-2008036765 A2 * | 3/2008 | ............ | A61K 48/00 |
| WO | 2013062931 A2 | 5/2013 | | |
| WO | 2015138803 A1 | 9/2015 | | |
| WO | 2015153679 A1 | 10/2015 | | |
| WO | 2016049045 A1 | 3/2016 | | |

OTHER PUBLICATIONS

Kitazono et al. Pancreas. 2013. 42(7):1120-1128. (Year: 2013).*
Matthaei et al. Clin Cancer Res. 2012. 18(17):4713-4724 and Supplementary Materials. (Year: 2012).*
Sato et al. Clin Cancer Res. 2005. 11(13):4681-4688. (Year: 2005).*
Szafranska et al. Clinical Chemistry. 2008. 54(10):1716-1724. (Year: 2008).*
Jiao et al. PLoS ONE. 2012. 7(2):e32068. (Year: 2012).*
Maker et al. J Am Coll Surg. 2019. 228(5)721-729. (Year: 2019).*
Extended European Search Report dated Dec. 14, 2020 for EP 18775545.9, filed Mar. 29, 2018.
Maker et al. (2010) "Cyst fluid mucin levels predict dysplasia in intraductal papillary mucinous neoplasms of the pancreas (IPMN)," Ann Surg Oncol. 17(1):1-139, Abstract 11.
Permuth-Wey et al. (2015) "A Genome-Wide Investigation of MicroRNA Expression Identifies Biologically-Meaningful MicroRNAs That Distinguish between High-Risk and Low-Risk Intraductal Papillary Mucinous Neoplasms of the Pancreas," PLoS ONE 10(1):e0116869-1.
TULLA & Maker (2017) "Can we better predict the biologic behavior of incidental IPMN? A comprehensive analysis of molecular diagnostics and biomarkers in intraductal papillary mucinous neoplasms of the pancreas," Langenbeck's Arch. Surg. 403(2):151-194.
Maker, A.V., N. Katabi, M. Gonen, R.P. DeMatteo, M.I. D'Angelica, Y. Fong, W.R. Jarnagin, M.F. Brennan and P.J. Allen (2011) "Pancreatic Cyst Fluid and Serum Mucin Levels Predict Dysplasia in Intraductal Papillary Mucinous Neoplasms of the Pancreas," Ann. Surg. Oncol. 18(1):199-206.
Maker, A.V., N. Katabi, L.-X. Qin, D.S. Klimstra, M. Schattner, M.F. Brennan, W.R. Jamagin and P.J. Allen (2011) "Cyst Fluid Interleukin-1b (IL1b) Levels Predict the Risk of Carcinoma in Intraductal Papillary Mucinous Neoplasms of the Pancreas," Clin. Cancer Res. 17(6):1502-1508.
Maker, A.V., S. Carrara, N.B. Jamieson, M. Palaez-Luna, A.M. Lennon, M. Dal Molin, A. Scarpa, L. Frulloni, W.R. Brugge (2015) "Cyst Fluid Biomarkers for Intraductal Papillary Mucinous Neoplasms of the Pancreas: A Critical Review from the International Expert Meeting on Pancreatic Branch-Duct-Intraductal Papillary Mucinous Neoplasms," J. Am. Coll. Surg. 220(2):243-253.
International Search Report and Written Opinion in PCT/US2018/025027 dated Jul. 23, 2018.
International Preliminary Report on Patentability in PCT/US2018/025027 dated Oct. 1, 2019.

(Continued)

*Primary Examiner* — Joseph G. Dauner
(74) *Attorney, Agent, or Firm* — Licata & Tyrrell P.C.

(57) ABSTRACT

A nucleic acid-based assay of pancreatic cyst fluid is provided for differentiating between high-grade and low-grade intraductal papillary mucinous neoplasms.

12 Claims, 1 Drawing Sheet
Specification includes a Sequence Listing.

(56) References Cited

OTHER PUBLICATIONS

Carrara, S. et al. (2011) "Mucin expression pattern in pancreatic diseases: findings from EUS-guided fine-needle aspiration biopsies," Am. J Gastroenterol. 106(7):1359-63.

* cited by examiner

SEQUENCE LISTING

<160> NUMBER OF SEQ ID NOS: 63

<210> SEQ ID NO 1
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 1
ggaagtacac gatgcggaga ct                                    22

<210> SEQ ID NO 2
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 2
accttcctca gctccgtctc tt                                    22

<210> SEQ ID NO 3
<211> LENGTH: 26
<212> TYPE: DNA
<213> ORGANISM: Artificial Sequence
<220> FEATURE:
<223> OTHER INFORMATION: Synthetic oligonucleotide

<400> SEQUENCE: 3
aacgggaagc ttgtcatcaa tggaaa                                26

<210> SEQ ID NO 4
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 4
gcatcagcag agggggcaga g                                     21

```
<210> SEQ ID NO 5
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 5
gcagacagat gcgcaaagaa gc                                              22

<210> SEQ ID NO 6
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 6
gcttttacca gattctccag cac                                             23

<210> SEQ ID NO 7
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 7
ccacagacct tccaggagaa tg                                              22

<210> SEQ ID NO 8
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 8
gtgcagttca gtgatcgtac agg                                             23

<210> SEQ ID NO 9
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 9
cagtagacac aaaacaggct cag                                             23

<210> SEQ ID NO 10
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 10
tgtcggatct ccctcaccaa tg                                              22

<210> SEQ ID NO 11
<211> LENGTH: 23
<212> TYPE: DNA
<213> ORGANISM: Artificial Sequence
<220> FEATURE:
<223> OTHER INFORMATION: Synthetic oligonucleotide
```

<400> SEQUENCE: 11
cctaccatcc tatgagcgag tac                                          23

<210> SEQ ID NO 12
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 12
gctgggtttg tgtaagagag gc                                           22

<210> SEQ ID NO 13
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 13
actctccaca cccagcatca tc                                           22

<210> SEQ ID NO 14
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 14
gtgtctccgt atgtgccgtt gt                                           22

<210> SEQ ID NO 15
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 15
aacacagcct gctagtccag ca                                           22

<210> SEQ ID NO 16
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 16
tggagaggat ggcttggtag gt                                           22

<210> SEQ ID NO 17
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 17
ccactggttc tatggcaaca cc                                           22

<210> SEQ ID NO 18
<211> LENGTH: 20

```
<212> TYPE: DNA
<213> ORGANISM: Artificial Sequence
<220> FEATURE:
<223> OTHER INFORMATION: Synthetic oligonucleotide

<400> SEQUENCE: 18
gccgaagtcc aggctgtgcg                                                    20

<210> SEQ ID NO 19
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 19
ccttctgcaa ctacaccagc tc                                                 22

<210> SEQ ID NO 20
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 20
tctctggtgg agctgaggaa ga                                                 22

<210> SEQ ID NO 21
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 21
ccttcaaggt tctgtgctca gc                                                 22

<210> SEQ ID NO 22
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 22
catcagctta gctggacact gc                                                 22

<210> SEQ ID NO 23
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 23
gaccacctca ttctcctggc ta                                                 22

<210> SEQ ID NO 24
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 24
```

```
aacctaagag cttggaggtc cc                                            22
```

<210> SEQ ID NO 25
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 25

```
cctctatgag gctgctgaca ag                                            22
```

<210> SEQ ID NO 26
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 26

```
atcacacgca gcacgccata ca                                            22
```

<210> SEQ ID NO 27
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 27

```
gatgagcagc ttttccagac gac                                           23
```

<210> SEQ ID NO 28
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 28

```
aactggacac cgaacagcag ct                                            22
```

<210> SEQ ID NO 29
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 29

```
caggaagaca gagtgtgctg gt                                            22
```

<210> SEQ ID NO 30
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 30

```
aattggacgg cggttcatcc ct                                            22
```

<210> SEQ ID NO 31
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 31
ccgtagatcc gaacttg                                                    17

<210> SEQ ID NO 32
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 32
gaacatgtct gcgtatctc                                                  19

<210> SEQ ID NO 33
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 33
aagtgctgac agtgcag                                                    17

<210> SEQ ID NO 34
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 34
gaacatgtct gcgtatctc                                                  19

<210> SEQ ID NO 35
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 35
cctgtagatc cgaatttg                                                   18

<210> SEQ ID NO 36
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 36
gaacatgtct gcgtatctc                                                  19

<210> SEQ ID NO 37
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 37
ggaatccctg tagtgtttcc tact                                            24

<210> SEQ ID NO 38
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 38
ccttgcatag tgcgcgtaat aa            22

<210> SEQ ID NO 39
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 39
tgctaatcgt gatagggg                 18

<210> SEQ ID NO 40
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 40
gaacatgtct gcgtatctc                19

<210> SEQ ID NO 41
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 41
agcttgaatt tactgcagtg aagg           24

<210> SEQ ID NO 42
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 42
aagaggactt cgcccgataa ct            22

<210> SEQ ID NO 43
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 43
aggtgcatct agtgcag                  17

<210> SEQ ID NO 44
<211> LENGTH: 19
<212> TYPE: DNA
<213> ORGANISM: Artificial Sequence
<220> FEATURE:
<223> OTHER INFORMATION: Synthetic oligonucleotide

```
<400> SEQUENCE: 44
gaacatgtct gcgtatctc                                            19

<210> SEQ ID NO 45
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 45
gcttatcaga ctgatgttg                                            19

<210> SEQ ID NO 46
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 46
gaacatgtct gcgtatctc                                            19

<210> SEQ ID NO 47
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 47
tactgcatca ggaactga                                             18

<210> SEQ ID NO 48
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 48
gaacatgtct gcgtatctc                                            19

<210> SEQ ID NO 49
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 49
ctttcagtcg gatgtttgca gc                                        22

<210> SEQ ID NO 50
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 50
catgccttga gtgtaggacc gt                                        22

<210> SEQ ID NO 51
```

```
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 51
tctcacacag aaatcgcacc cgt                                              23

<210> SEQ ID NO 52
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 52
gcctactgag ctgatatc                                                    18

<210> SEQ ID NO 53
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 53
gaacatgtct gcgtatctc                                                   19

<210> SEQ ID NO 54
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 54
gttgggatcg gttgcaa                                                     17

<210> SEQ ID NO 55
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 55
gaacatgtct gcgtatctc                                                   19

<210> SEQ ID NO 56
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 56
ccgtagaacc gaccttg                                                     17

<210> SEQ ID NO 57
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 57
```

```
gaacatgtct gcgtatctc                                              19
```

<210> SEQ ID NO 58
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 58

```
tggtcatcca gcaggtgttc ga                                          22
```

<210> SEQ ID NO 59
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 59

```
acagacactg gcaacattgc gg                                          22
```

<210> SEQ ID NO 60
<211> LENGTH: 32
<212> TYPE: DNA
<213> ORGANISM: Artificial Sequence
<220> FEATURE:
<223> OTHER INFORMATION: Synthetic oligonucleotide

<400> SEQUENCE: 60

```
tggtggagta tttgatagtg tattaacctt at                               32
```

<210> SEQ ID NO 61
<211> LENGTH: 31
<212> TYPE: DNA
<213> ORGANISM: Artificial Sequence
<220> FEATURE:
<223> OTHER INFORMATION: Synthetic oligonucleotide

<400> SEQUENCE: 61

```
aaacaagatt tacctctatt gttggatcat a                                31
```

<210> SEQ ID NO 62
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 62

```
tctgagccct ctttccaaac tac                                         23
```

<210> SEQ ID NO 63
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 63

```
ggactggggt gaatgtcaag aa                                          22
```

METHOD AND KIT FOR DIAGNOSING EARLY STAGE PANCREATIC CANCER

INTRODUCTION

This patent application is a U.S. National Stage Application of PCT/US2018/025027 filed Mar. 29, 2018 and claims benefit of priority from U.S. Provisional Patent Application Ser. No. 62/478,860, filed Mar. 30, 2017, the contents of each of which are hereby incorporated by reference in their entirety.

BACKGROUND

Intraductal papillary mucinous neoplasms of the pancreas (IPMNs) are tumors characterized by intraductal proliferation of neoplastic mucinous cells with various degrees of cytologic atypia, which usually form papillae and lead to cystic dilatation of pancreatic ducts, forming clinically detectable masses. Macroscopically, IPMN is classified into main-duct, combined, and branch-duct types based on the differential involvement of the pancreatic duct system. It has been shown that main-duct and combined-type IPMNs are more likely to have invasive carcinoma compared to branch-duct type (48% and 42% vs. 11%), and subsequently, 5-year disease-specific survival rates of main-duct and combined-type IPMNs are significantly lower than that of branch-duct type (65% and 77% vs. 91%). Histologically, IPMN are thought to progress from low-grade dysplasia (adenoma) to high-grade dysplasia (carcinoma in situ) and invasive carcinoma. While the 5-year survival of patients with resected non-invasive IPMN is as high as 77-94%, invasive IPMN carries a much poorer survival of 33-43%. Given the significant difference in survival between invasive and non-invasive IPMNs as well as between main-duct and branch-duct IPMNs, clinical guidelines have been adopted to assist clinicians in determining when a lesion should be surgically resected. However, while sensitive (97-100%), these guidelines have proven to be highly non-specific (23-30%), especially among branch-duct IPMN. Given the prevalence of asymptomatic cysts in an elderly population who tend to have comorbidity, more specific tools that can segregate high-risk and malignant from low-risk lesions are warranted. In an effort to improve diagnostic accuracy, analyses of cyst fluid for genetic changes have been used and several biomarkers including GNAS (Guanine Nucleotide Binding Protein (G Protein), Alpha), KRAS (GTPase KRAS proto-oncogene), IL1B, mucin and microRNAs have been suggested. See, US 2017/0022571; Maker, et al. (2011) *Ann. Surg. Oncol.* 18(1):199; Maker, et al. (2011) *Clin. Cancer Res.* 17(6):1502-8; Maker, et al. (2015) *J. Am. Coll. Surg.* 220(2):243-253. However, a combination of specific markers of clinically high-risk lesions are needed to aid in the pre-operative diagnosis and risk stratification of patients with IPMN.

SUMMARY OF THE INVENTION

This invention provides a method of differentiating between high-risk and low-risk intraductal papillary mucinous neoplasms and the level of cyst dysplasia by determining the expression levels of one or more biomarker messenger RNAs (mRNAs) or one or more biomarker microRNAs (miRNAs) in a sample of pancreatic cyst fluid; comparing the expression levels of the one or more biomarker mRNAs or one or more biomarker miRNAs to the expression level of the one or more biomarkers in a cyst fluid control sample; and classifying the sample as a high-risk or low-risk intraductal papillary mucinous neoplasm. In one embodiment, the mRNAs are selected from the group of ERBB2, GAPDH, GNAS, IL1B, KRAS, MUC-1, MUC-2, MUC-4, MUC-5AC, MUC-7, PGE2-R, PTGER2, PTGES2, PTGS1 and TP63. In another embodiment, the miRNAs are selected from the group of hsa-miR-101, hsa-miR-106b, hsa-miR-10a, hsa-miR-142-3p, hsa-miR-155, hsa-miR-17-3p, hsa-miR-18a, hsa-miR-21, hsa-miR-217, hsa-miR-24, hsa-miR-30a-3p, hsa-miR-342-3p, hsa-miR-532-3p, hsa-miR-92a and hsa-miR-99b. In a further embodiment, the mRNAs or biomarker miRNAs are three biomarkers selected from the group of hsa-miR-21, hsa-miR-342-3p, IL1B, KRAS, MUC-4, and PTGES2. In a particular embodiment, the biomarker mRNAs are IL1B, MUC4, and PTGES2. In yet a further, the method includes measuring the expression of one or more biomarker proteins, e.g., ERRB2, GAPDH, GNAS, IL1B, KRAS, MUC-1, MUC-2, MUC-4, MUC-SAC, MUC-7, PGE2-R and PTGER2. In addition, the method can include the step of normalizing the relative expression levels of the one or more biomarker miRNAs and mRNAs to a reference mRNA, e.g., RPLP0. A kit for differentiating between high-risk and low-risk intraductal papillary mucinous neoplasms and the level of cyst dysplasia is also provided, which includes primer sets for amplifying one or more biomarker mRNAs or one or more biomarker miRNAs in a sample of pancreatic cyst fluid.

DETAILED DESCRIPTION OF THE INVENTION

Figure 1:
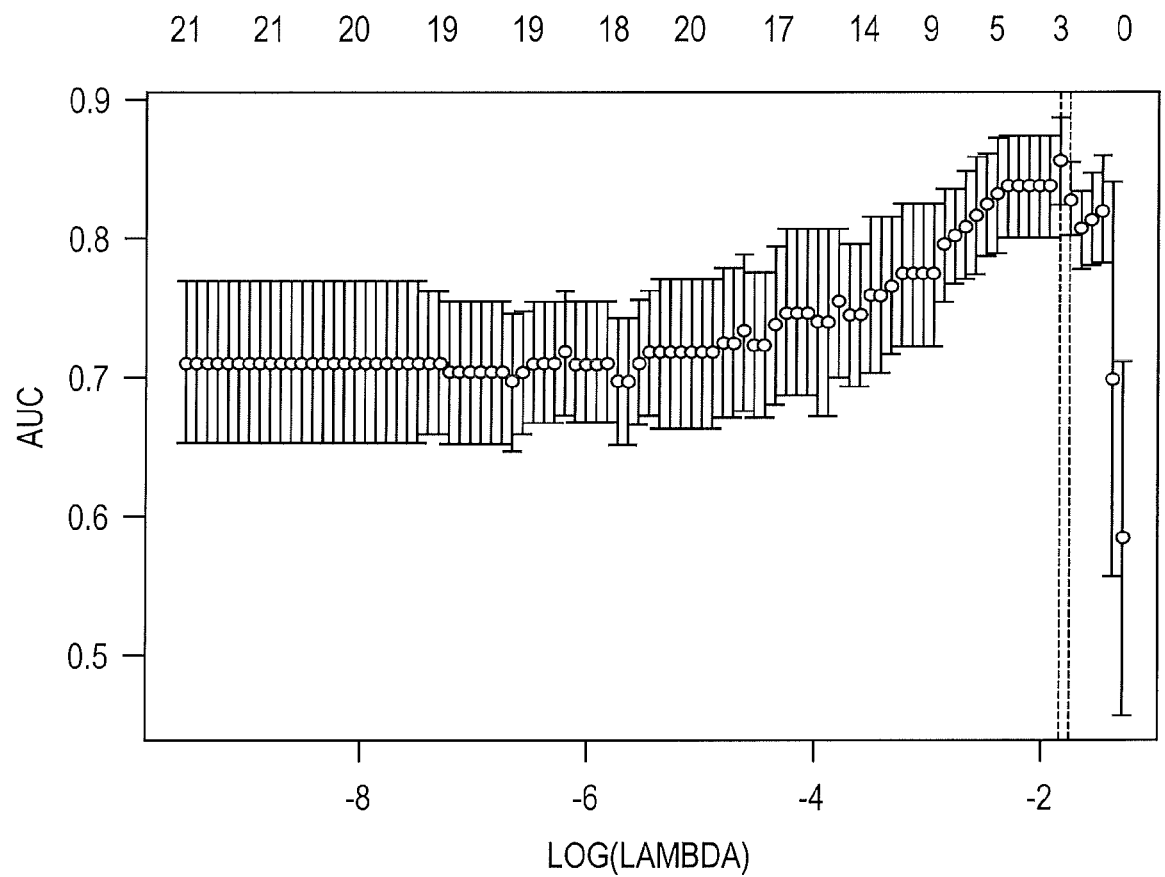
FIG. 1 shows Lasso penalized logistic regression with cross validation, which identified a three-gene cyst fluid signature with optimal accuracy to predict the risk of pancreatic malignancy in IPMN. In this model, low-risk (low and moderate grade dysplasia) versus high-risk (high-grade dysplasia and invasive cancer) cysts were predicted with an accuracy, as measured by AUC, of 86%; y=0.36+(−0.06 IL1B)+(−0.17 MUC4)+(−0.50 PTGES2); AUC=0.86, p-value=0.002.

An assay of pancreatic cyst fluid has now been developed as a diagnostic tool to identify patients with pre-malignant cysts of the pancreas that are at high risk for progressing to malignancy. The instant assay incorporates differentially expressed mRNA and miRNA, and optionally proteins, into a rapid and simple assay that can be performed on cyst fluid from patients with pathologically proven low-risk and high-risk (high grade dysplasia) IPMN to determine the risk of pancreatic cancer. The assay of this invention accurately discriminates high-risk cysts from low-risk cysts with an accuracy of 86% thereby by assisting clinicians in determining when a lesion should be surgically resected.

Accordingly, this invention is a method of differentiating between high-risk (invasive and high grade dysplasia) and low-risk (low and moderate grade dysplasia) intraductal papillary mucinous neoplasms by determining the expression levels of one or more biomarker mRNAs and one or more biomarker miRNAs in a sample of pancreatic cyst fluid; comparing the expression levels of the one or more biomarker mRNAs and one or more biomarker miRNAs to the expression level of the one or more biomarkers in a serous cyst fluid reference sample; and classifying the sample as a high-risk or low-risk intraductal papillary mucinous neoplasm based upon the expression level of the biomarkers compared to the reference.

"Intraductal papillary mucinous neoplasm" or "IPMN" refers to a type of tumor (neoplasm) that grows within the pancreatic ducts (intraductal) and is characterized by the production of thick fluid by the tumor cells (mucinous). Intraductal papillary mucinous neoplasms are important because if they are left untreated some of them progress to invasive cancer (transform from a benign tumor to a malignant tumor). The histologic grade of IPMN is based on the highest level of dysplasia present in the lesion. This can be determined by cytologic sample obtained from cyst fluid or wall during EUS-FNA or core biopsy. Criteria for cytologic atypia included at least 1 of the following: increased nuclear-cytoplasmic ratio, increased nuclear size, nuclear crowding, or hyperchromasia. Ultimately this is determined via pathologic analysis of a permanently prepared surgical pancreas specimen. The histologic grades are defined in the following ways: adenoma (dilated pancreatic duct lined by mucinous epithelium, with <1 criteria for low-grade dysplasia; also called duct ectasia), moderate (>2 of the following criteria: epithelial tufuting, nuclear pseudostratification, nuclear atypia, and mitotic figures; also called borderline), high-grade dysplasia (cribiform or solid growth usually associated with high grade nuclear atypical; also called non-invasive intraductal carcinoma or carcinoma in situ), and invasive (disruption of the ductal basement membrane and extension of dysplastic cells into the pancreatic tissue with or without lymphovascular invasion.

Additional information on the identification, categorization and characterization of pancreatic lesions including pancreatic cysts as it is currently practice in the surgical arts can be found in treatises such as, *Current Surgical Therapy*, edited by John L. Cameron (9$^{th}$ ed, 1397 pp, Philadelphia, Pa., Mosby/Elsevier, 2008), and similar texts, reviews, manuals and papers known in the art. Samples of use in the method of this invention may be obtained by endoscopic ultrasound guided fine needle fluid aspiration, duodenal fluid collection, pancreatic duct aspiration, or direct collection of cyst fluid during operation.

For the purposes of this invention, "high-risk IPMN" refers to invasive and high-grade dysplasia IPMN, whereas "low-risk IPMN" refers to low- and moderate-grade dysplasia. Ideally, the method of this invention distinguishes high-risk IPMN from low-risk IPMN to identify patients that are at high risk for progressing to malignancy.

A biomarker is an organic biomolecule, the presence of which in a pancreatic fluid sample has been shown to classify the sample as a high-risk or low-risk IPMN the progressing to malignancy. In a preferred embodiment, the biomarker is differentially expressed in a sample taken from a subject of one phenotypic status (e.g., having high-risk IPMN) as compared with another phenotypic status (e.g., having low-risk IPMN). When assessed in combination, the biomarkers of this invention provide for determining whether a subject belongs to one phenotypic status or another. Therefore, they are useful as markers for disease (diagnostics), therapeutic effectiveness of a drug (theranostics), drug toxicity, and selecting a suitable treatment (e.g., surgical intervention) for a subject.

mRNA Biomarkers

As is conventional in the art, an mRNA or messenger RNA is a subtype of RNA that encodes the amino acid sequence of a protein. The method of the invention includes determining or measuring in a sample from the patient expression levels of one, two, three, four, five, six, seven, eight, nine, or more biomarker mRNA selected from the group of ERBB2, GAPDH, GNAS, IL1B, KRAS, MUC-1, MUC-2, MUC-4, MUC-5AC, MUC-7, PGE2-R, PTGER2, PTGES2, PTGS1 and/or TP63. These mRNAs are known in the art under the GENBANK Accession numbers presented in TABLE 1.

TABLE 1

| mRNA | Gene | Accession No. |
|---|---|---|
| ERBB2 | Erb-B2 Receptor Tyrosine Kinase 2 | NM_004448 |
| GAPDH | Glyceraldehyde-3-Phosphate Dehydrogenase | NM_002046 |
| GNAS | Guanine Nucleotide Binding Protein (G Protein), Alpha | NM_000516 |
| IL1B | Interleukin 1 Beta | NM_000576 |
| KRAS | GTPase KRAS proto-oncogene | NM_033360 NM_004985 |
| MUC-1 | Mucin 1 | NM_002456 |
| MUC-2 | Mucin 2 | NM_002457 |
| MUC-4 | Mucin 4 | NM_018406 |
| MUC-5AC | Mucin 5AC | NM_017511 |
| MUC-7 | Mucin 7 | NM_152291 |
| PGE2-R | Prostaglandin E2 receptor | NM_000957 |
| PTGER2 | Prostaglandin E Receptor 2 (Subtype EP2) | NM_000956 |
| PTGES2 | Prostaglandin E Synthase 2 | NM_025072 |
| PTGS1 | Prostaglandin-Endoperoxide Synthase 1 | NM_000962 |
| TP63 | Tumor Protein p63 | NM_003722 |

In some embodiments, a level of mRNA is increased or decreased compared to a control or reference level if it is at least 20, 30, 40, 50, 60, 80, 90, 100, 110, 120, 130, 140, 150, 160, 170, 180, 190, 200, 250, 300, 350, 400, 450, 500, 600, 700, 800, 900, or 1000% higher or lower (or any range derivable therein) than the reference or control level. This may or may not include using a standardized or normalized level of expression in determining whether there is an increase or decrease.

miRNA Biomarkers

MicroRNAs (miRNAs) are non-coding RNA molecules of approximately 21-23 nucleotides in length that regulate target gene expression by interfering with their transcription or by inhibiting translation. The method of the invention further includes determining or measuring in a sample from the patient expression levels of one, two, three, four, five, six, seven, eight, nine, or more biomarker miRNA selected from the group of hsa-miR-101, hsa-miR-106b, hsa-miR-10a, hsa-miR-142-3p, hsa-miR-155, hsa-miR-17-3p, hsa-miR-18a, hsa-miR-21, hsa-miR-217, hsa-miR-24, hsa-miR-30a-3p, hsa-miR-342-3p, hsa-miR-532-3p, hsa-miR-92a and/or hsa-miR-99b. These miRNAs are known in the art under the Accession numbers presented in TABLE 2.

TABLE 2

| hsa-miR | Accession No. |
|---|---|
| 101 | MIMAT0000098 |
| 106b | MIMAT0000680 |
| 10a | MIMAT0000253 |
| 142-3p | MIMAT0000434 |
| 155 | MIMAT0000646 |
| 17-3p | MIMAT0000071 |
| 18a | MIMAT0000072 |
| 21 | MIMAT0000076 |
| 217 | MIMAT0000274 |
| 24 | MIMAT0000079 |
| 30a-3p | MIMAT0000088 |

TABLE 2-continued

| hsa-miR | Accession No. |
|---|---|
| 342-3p | MIMAT0000753 |
| 532-3p | MIMAT0004780 |
| 92a | MIMAT0004507 |
| 99b | MIMAT0000689 |

In some embodiments, a level of miRNA is increased or decreased compared to a control or reference level if it is at least 20, 30, 40, 50, 60, 80, 90, 100, 110, 120, 130, 140, 150, 160, 170, 180, 190, 200, 250, 300, 350, 400, 450, 500, 600, 700, 800, 900, or 1000% higher or lower (or any range derivable therein) than the reference or control level. This may or may not include using a standardized or normalized level of expression in determining whether there is an increase or decrease.

Protein Biomarkers

In some embodiments, the method of the invention further includes determining or measuring in a sample from the patient expression levels of one, two, three, four, five, six, seven, eight, nine, or more biomarker proteins selected from the group of ERRB2, GAPDH, GNAS, IL1B, KRAS, MUC-1, MUC-2, MUC-4, MUC-5AC, MUC-7, PGE2-R and/or PTGER2. These proteins are known in the art under the GENBANK Accession numbers presented in TABLE 3.

TABLE 3

| Protein | GENBANK Accession No. |
|---|---|
| ERBB2 | NP_004439 |
| GAPDH | NP_002037 |
| GNAS | NP_000507 |
| IL1B | NP_000576 |
| KRAS | NP_203524 |
|  | NP_004976 |
| MUC-1 | NP_002447 |
| MUC-2 | NP_002448 |
| MUC-4 | NP_060876 |
| MUC-5AC | NP_059981 |
| MUC-7 | NP_001138478 |
| PGE2-R | NP_000948 |
| PTGER2 | NP_000947 |

Using the biomarker(s) described herein, the present invention provides a method for differentiating, diagnosing and treating high-risk IPMN by measuring the expression level of one or more biomarker mRNAs and/or one or more biomarker miRNAs in a sample of pancreatic cyst fluid, and optionally one or more biomarker proteins. Ideally, the expression level of biomarker mRNAs and miRNAs in a sample of pancreatic cyst fluid is measured thereby providing an assay consisting of measuring the expression of nucleic acids (i.e., nucleic acid-based). As used in the context of the present invention, a sample of pancreatic cyst fluid includes cells, nucleic acids, proteins, and/or membrane extracts of cells and may be obtained from a subject (e.g., human, livestock or companion animal) according to standard clinical practices.

The levels or amounts of biomarker mRNA and miRNA in a sample are determined by measuring the level or amount of these nucleic acid molecules. Nucleic acid biomarkers can be detected using any available method including, but not limited to, northern blot analysis, nuclease protection assays (NPA), Serial Analysis of Gene Expression (SAGE), RNA Seq, in situ hybridization, reverse-transcriptase PCR (RT-PCR), PCR, quantitative RT-PCR (qRT-PCR), microarray, tiling arrays and the like. Due to the ease of use, it is generally desirable to detect the nucleic acid molecules using a PCR-based approach. In general, this involves contacting the sample with two or more PCR primers, which specifically hybridize with nucleic acids of the biomarker, subjecting the sample to multiple steps of PCR amplification and detecting the amount of the amplified sequence (e.g., using gel analysis, blotting methods, fluorescently labeled probes and/or incorporation of a fluorescent dye that intercalates double stranded DNA such as SYBR® Green). Alternatively, an oligonucleotide, an aptamer, a cDNA, an antibody, or a fragment thereof, which interacts with at least a portion of the biomarker nucleic acid is configured in an array on a chip or wafer and used for detecting biomarker nucleic acids. Briefly, these techniques involve methods for analyzing large numbers of genes rapidly and accurately. By tagging genes with oligonucleotides or using fixed probe arrays, one can employ chip technology to segregate target molecules as high density arrays and screen these molecules on the basis of hybridization (see, e.g., Pease, et al. (1994) *Proc. Natl. Acad. Sci. USA* 91(11):5022-6; Fodor, et al. (1991) *Science* 251(4995):767-73).

Primers (e.g., for PCR-based approaches), probes (e.g., for hybridization-based approaches) or oligonucleotides (e.g., for microarray-based approaches) for use in this embodiment can be selected from any region of the biomarker nucleic acid (see Tables 1 and 2) and generally specifically anneal and amplify at least a portion of a biomarker nucleic acid molecule and no other nucleic acid molecule encoding a closely related molecule. Suitable primers for amplification of biomarker nucleic acid molecules can be selected by analyzing the sequences provided by the sequences disclosed herein.

In general, suitable primers are 12 to 30 bp in length and generate a PCR amplicon of 50, 100, 200 400, 600, 1000 bp or more in length. In accordance with this method, a geometrically amplified product is obtained only when the first and second nucleotide sequences occur within the same biomarker nucleic acid molecule. The fundamentals of non-degenerate PCR are known to the skilled artisan, see, e.g. McPherson, et al., PCR, A Practical Approach, IRL Press, Oxford, Eng. (1991).

Exemplary oligonucleotides, forward and reverse primers, or probes for in assessing mRNA expression are provided in Table 4. However, other suitable oligonucleotides/primers/probes are well-known in the art and available from commercial sources such as Sino Biological, Bio-Rad, OriGene, R&D Systems and the like.

TABLE 4

| mRNA | Oligo | Sequence (5'->3') | SEQ ID NO: |
|---|---|---|---|
| ERBB2 | Forward | GGAAGTACACGATGCGGAGACT | 1 |
|  | Reverse | ACCTTCCTCAGCTCCGTCTCTT | 2 |
| GAPDH | Forward | AACGGGAAGCTTGTCATCAATGGAAA | 3 |
|  | Reverse | GCATCAGCAGAGGGGCAGAG | 4 |
| GNAS | Forward | GCAGACAGATGCGCAAAGAAGC | 5 |
|  | Reverse | GCTTTTACCAGATTCTCCAGCAC | 6 |
| IL1B | Forward | CCACAGACCTTCCAGGAGAATG | 7 |
|  | Reverse | GTGCAGTTCAGTGATCGTACAGG | 8 |
| KRAS | Forward | CAGTAGACACAAAACAGGCTCAG | 9 |
|  | Reverse | TGTCGGATCTCCCTCACCAATG | 10 |
| MUC-1 | Forward | CCTACCATCCTATGAGCGAGTAC | 11 |
|  | Reverse | GCTGGGTTTGTGTAAGAGAGGC | 12 |

TABLE 4-continued

| mRNA | Oligo | Sequence (5'->3') | SEQ ID NO: |
|---|---|---|---|
| MUC-2 | Forward | ACTCTCCACACCCAGCATCATC | 13 |
|  | Reverse | GTGTCTCCGTATGTGCCGTTGT | 14 |
| MUC-4 | Forward | AACACAGCCTGCTAGTCCAGCA | 15 |
|  | Reverse | TGGAGAGGATGGCTTGGTAGGT | 16 |
| MUC-5AC | Forward | CCACTGGTTCTATGGCAACACC | 17 |
|  | Reverse | GCCGAAGTCCAGGCTGTGCG | 18 |
| MUC-7 | Forward | CCTTCTGCAACTACACCAGCTC | 19 |
|  | Reverse | TCTCTGGTGGAGCTGAGGAAGA | 20 |
| PGE2-R | Forward | CCTTCAAGGTTCTGTGCTCAGC | 21 |
|  | Reverse | CATCAGCTTAGCTGGACACTGC | 22 |
| PTGER2 | Forward | GACCACCTCATTCTCCTGGCTA | 23 |
|  | Reverse | AACCTAAGAGCTTGGAGGTCCC | 24 |
| PTGES2 | Forward | CCTCTATGAGGCTGCTGACAAG | 25 |
|  | Reverse | ATCACACGCAGCACGCCATACA | 26 |
| PTGS1 | Forward | GATGAGCAGCTTTTCCAGACGAC | 27 |
|  | Reverse | AACTGGACACCGAACAGCAGCT | 28 |
| TP63 | Forward | CAGGAAGACAGAGTGTGCTGGT | 29 |
|  | Reverse | AATTGGACGGCGGTTCATCCCT | 30 |

Exemplary oligonucleotides, forward and reverse primers, or probes for in assessing miRNA expression are provided in Table 5. However, other suitable oligonucleotides/primers/probes are well-known in the art and available from commercial sources such as Sino Biological, Bio-Rad, OriGene, R&D Systems and the like.

TABLE 5

| hsa-miR | Oligo | Sequence (5'->3') | SEQ ID NO: |
|---|---|---|---|
| 101 | Forward | CCGTAGATCCGAACTTG | 31 |
|  | Reverse | GAACATGTCTGCGTATCTC | 32 |
| 106b | Forward | AAGTGCTGACAGTGCAG | 33 |
|  | Reverse | GAACATGTCTGCGTATCTC | 34 |
| 10a | Forward | CCTGTAGATCCGAATTTG | 35 |
|  | Reverse | GAACATGTCTGCGTATCTC | 36 |
| 142-3p | Forward | GGAATCCCTGTAGTGTTTCCTACT | 37 |
|  | Reverse | CCTTGCATAGTGCGCGTAATAA | 38 |
| 155 | Forward | TGCTAATCGTGATAGGGG | 39 |
|  | Reverse | GAACATGTCTGCGTATCTC | 40 |
| 17-3p | Forward | AGCTTGAATTTACTGCAGTGAAGG | 41 |
|  | Reverse | AAGAGGACTTCGCCCGATAACT | 42 |
| 18a | Forward | AGGTGCATCTAGTGCAG | 43 |
|  | Reverse | GAACATGTCTGCGTATCTC | 44 |
| 21 | Forward | GCTTATCAGACTGATGTTG | 45 |
|  | Reverse | GAACATGTCTGCGTATCTC | 46 |
| 217 | Forward | TACTGCATCAGGAACTGA | 47 |
|  | Reverse | GAACATGTCTGCGTATCTC | 48 |
| 30a-3p | Stem Loop | CTTTCAGTCGGATGTTTGCAGC | 49 |
| 532-3p | Stem Loop | CATGCCTTGAGTGTAGGACCGT | 50 |
| 342-3p | Stem Loop | TCTCACACAGAAATCGCACCCGT | 51 |
| 24 | Forward | GCCTACTGAGCTGATATC | 52 |
|  | Reverse | GAACATGTCTGCGTATCTC | 53 |
| 92a | Forward | GTTGGGATCGGTTGCAA | 54 |
|  | Reverse | GAACATGTCTGCGTATCTC | 55 |
| 99b | Forward | CCGTAGAACCGACCTTG | 56 |
|  | Reverse | GAACATGTCTGCGTATCTC | 57 |

The expression of biomarker proteins is measured in assays using a binding agent, which specifically binds to the biomarker protein and no other protein. In this embodiment, a sample is contacted with a binding agent (e.g., antibody), which binds the biomarker protein, and the resulting biomarker-binding agent complex is detected using standard assays (e.g., an immunoassay). When the binding agent is, for example, a peptide aptamer, the biomarker-binding agent complex can be directly detected by, for example, a detectable marker protein (e.g., β-galactosidase, GFP or luciferase) fused to the aptamer. Subsequently, the level or amount of the biomarker-binding agent complex is correlated with the expression of level of the biomarker protein in the sample.

Binding agents for use in accordance with the instant invention include antibodies or antibody fragments, as well as peptide aptamers. In particular embodiments of the invention, the binding agent specifically recognizes a biomarker protein listed in Table 3. When the binding agent is an antibody, the antibody can be purchased from a commercial source. Alternatively, an antibody that specifically binds to or recognizes a biomarker protein can be raised against an antigen fragment of the biomarker protein. Suitable antigenic regions can be readily identified by the skilled artisan using any art-established computer algorithm for identifying such antigenic sequences (e.g., Jamison and Wolf (1988) *Bioinformatics* 4:181-186; Carmenes, et al. (1989) *Biochem Biophys Res Commun.* 159(2):687-93).

For the production of antibodies, various hosts including goats, rabbits, rats, mice, humans, and others, may be immunized by injection with a biomarker protein or any fragment or oligopeptide thereof which has antigenic or immunogenic properties. Depending on the host species, various adjuvants can be used to increase the immunological response. Such adjuvants include, but are not limited to, Freund's, mineral gels such as aluminum hydroxide, and surface-active substances such as lysolecithin, PLURONIC® polyols, polyanions, peptides and oil emulsions. Among adjuvants used in humans, BCG (bacilli Calmette-Guerin) and *Corynebacterium parvum* are particularly suitable.

An antibody to a biomarker protein can be generated by immunizing an animal with an oligopeptide, peptide, or fragment of the biomarker protein. Generally, such oligopeptides, peptides, or fragments have an amino acid sequence composed of at least five amino acid residues and more desirably at least 10 amino acid residues. Fragments of a biomarker protein can be generated by, for example, tryptic digestion and extraction from a preparative SDS-PAGE gel or by recombinant fragment expression and purification. Further, short stretches of amino acids of the biomarker antigen can be fused with those of another protein such as keyhole limpet hemocyanin and antibody produced against the chimeric molecule.

Monoclonal antibodies to a biomarker protein can be prepared using any technique which provides for the production of antibody molecules by continuous cell lines in culture. These include, but are not limited to, the hybridoma technique, the human B-cell hybridoma technique, and the EBV-hybridoma technique (Kohler, et al. (1975) *Nature* 256:495-497; Kozbor, et al. (1985) *J. Immunol. Methods* 81:31-42; Cote, et al. (1983) *Proc. Natl. Acad. Sci.* 80:2026-2030; Cole, et al. (1984) *Mol. Cell Biol.* 62:109-120).

Moreover, antibodies to a biomarker protein can be isolated by screening libraries of antibodies or antibody-like molecules, such as Forkhead-Associated (FHA) domains, monobodies, minibodies, AFFIBODY® molecules, AFFILINS®, ANTICALINS®, DARPins® (i.e., designed ankyrin repeat proteins), and NANOFITINS® (also known as affitins). Library platforms for screening for antibodies or antibody-like molecules include, but are not limited to, phage display (see, e.g., Benhar & Reiter (2002) *Curr. Protoc. Immunol.* 48:VI:10.19B:10.19B.1-10.19B.31), yeast display (see, e.g., Miller, et al. (2005) *Prot. Expr. Purif.* 42:255-67), and ribosome display (see, e.g., Douthwaite, et al. (2006) *Prot. Eng. Des. Sel.* 19:85-90).

In addition, techniques developed for the production of humanized and chimeric antibodies, the splicing of mouse antibody genes to human antibody genes to obtain a molecule with appropriate antigen specificity and biological activity, can be used (Morrison, et al. (1984) *Proc. Natl. Acad. Sci.* 81, 6851-6855; Neuberger, et al. (1984) *Nature* 312:604-608; Takeda, et al. (1985) *Nature* 314:452-454). Alternatively, techniques described for the production of single chain antibodies can be adapted, using methods known in the art, to produce specific single chain antibodies. Antibodies with related specificity, but of distinct idiotypic composition, can be generated by chain shuffling from random combinatorial immunoglobulin libraries (Burton (1991) *Proc. Natl. Acad. Sci.* 88:11120-11123).

Antibodies can also be produced by inducing in vivo production in the lymphocyte population or by screening immunoglobulin libraries or panels of highly specific binding reagents as is well-known in the art (Orlandi, et al. (1989) *Proc. Natl. Acad. Sci.* 86: 3833-3837; Winter, et al. (1991) *Nature* 349:293-299).

Antibodies of use in the method herein include, but are not limited to, polyclonal, monoclonal, chimeric, single chain, Fab fragments, bispecific scFv fragments, Fd fragments and fragments produced by a Fab expression library. For example, fragments include, but are not limited to, the F(ab')$_2$ fragments which can be produced by pepsin digestion of the antibody molecule and the Fab fragments which can be generated by reducing the disulfide bridges of the F(ab')$_2$ fragments. Alternatively, Fab expression libraries can be constructed to allow rapid and easy identification of monoclonal Fab fragments with the desired specificity (Huse, et al. (1989) *Science* 254:1275-1281).

Diabodies are also contemplated. A diabody refers to an engineered antibody construct prepared by isolating the binding domains (both heavy and light chain) of a binding antibody, and supplying a linking moiety which joins or operably links the heavy and light chains on the same polypeptide chain thereby preserving the binding function (see, Holliger et al. (1993) *Proc. Natl. Acad. Sci. USA* 90:6444; Poljak (1994) *Structure* 2:1121-1123). This forms, in essence, a radically abbreviated antibody, having only the variable domain necessary for binding the antigen. By using a linker that is too short to allow pairing between the two domains on the same chain, the domains are forced to pair with the complementary domains of another chain and create two antigen-binding sites. These dimeric antibody fragments, or diabodies, are bivalent and bispecific. It should be clear that any method to generate diabodies, as for example described by Holliger, et al. (1993) supra, Poljak (1994) supra, Zhu, et al. (1996) *Biotechnology* 14:192-196, and U.S. Pat. No. 6,492,123, herein incorporated by reference, can be used.

Various immunoassays can be used for measuring binding of a binding agent to a biomarker protein and hence determining the expression of the biomarker protein. Numerous protocols for competitive binding (e.g., ELISA), latex agglutination assays, sandwich immunoassays, gel diffusion reactions, in situ immunoassays, immunoradiometric assays, western blot analyses, slot blot assays and kinetics (e.g., BIACORE™ analysis) using either polyclonal or monoclonal antibodies, or fragments thereof, are well-known in the art. Such immunoassays typically involve the measurement of complex formation between a specific antibody and its cognate antigen. A two-site, monoclonal-based immunoassay utilizing monoclonal antibodies reactive to two non-interfering epitopes is suitable, but a competitive binding assay can also be employed. For a review of the general immunoassays, see also, *Methods in Cell Biology: Antibodies in Cell Biology* (1993) Asai, ed. volume 37; *Basic and Clinical Immunology* (1991) Stites & Teff, eds. 7th ed.).

In one embodiment, protein marker analysis involves the use of a primary antibody that specifically binds to the marker protein. In certain embodiments, antibody binding is detected by detecting a label on the primary antibody. In another embodiment, the primary antibody is detected by detecting binding of a secondary antibody or reagent to the primary antibody. In a further embodiment, the secondary antibody is labeled.

In some embodiments, an automated detection assay is used. Methods for the automation of immunoassays are well-known in the art and may be employed in this invention. In some embodiments, the analysis and presentation of results is also automated. For example, in some embodiments, software that generates a prognosis based on the presence or absence of a series of proteins corresponding to cancer markers is used.

Peptide aptamers that specifically bind to a biomarker protein can be rationally designed or screened for in a library of aptamers (e.g., provided by Aptanomics SA, Lyon, France). In general, peptide aptamers are synthetic recognition molecules whose design is based on the structure of antibodies. Peptide aptamers are composed of a variable peptide loop attached at both ends to a protein scaffold. This double structural constraint greatly increases the binding affinity of the peptide aptamer to levels comparable to that of an antibody (nanomolar range). Likewise, aptamers, which bind to nucleic acid sequences encoding a biomarker protein, can also be identified in library screens.

Using the method of the invention, expression levels of mRNA and miRNA biomarkers are determined in a sample from a subject with pancreatic cancer. To minimize the effect of sample-to-sample variation, the method is usually performed using an internal standard, or one or more reference miRNAs. The ideal internal standard is expressed at a constant level among different tissues, and is unaffected by the experimental treatment. RNAs that can be used to normalize patterns of expression include, e.g., mRNAs for the reference genes β-actin, GUSB, RPLP0 and TFRC. See, e.g., Eisenberg and Levanon (2003) *Trends in Genetics* 19:362, for a list of additional suitable reference genes. In certain embodiments, the levels of biomarker mRNAs and miRNAs in a sample from a patient are assayed by a quantitative method, and said levels are then "normalized" relative to the level of expression of the mRNA of one of more reference mRNAs, thereby generating a normalized expression level of the biomarkers. In certain embodiments, the reference mRNA is RPLP0 (Ribosomal Protein Lateral Stalk Subunit P0; GENBANK Accession No. NM_001002).

By way of illustration, the level of mRNA or miRNA as measured by TaqMan® RT-PCR is referred to as the cycle threshold (Ct) value. The lower the Ct, the greater the amount of RNA present in the sample. The expression value of a mRNA or miRNA in a sample is normalized, e.g., by first determining the mean expression value in Ct of the designated reference mRNA in a sample ($Ct_{Ref}$). The normalized expression value for a biomarker ($Ct_{Biomarker}$) is then calculated as $Ct_{Biomarker} = (C_t)(Ct_{Ref})$. Optionally, the normalized expression values for all biomarkers can be adjusted, e.g., so that all adjusted normalized Ct have a value >0. In certain embodiments, biomarker expression levels are processed to obtain relative quantitative (RQ) values that are z-transformed, log2 transformed, and scaled (X-mean/standard deviation). See, e.g., Cheadle, et al. (2003) *J. Mol. Diagn.* 5:73-81. In addition, the expression of each of the biomarkers may be weighted based on the ability of the biomarker to predict a high risk or a low risk IPMN.

After a normalized biomarker expression level is determined, it is compared to expression levels of the same biomarker in a serous cyst fluid control sample. Based upon these comparisons, the sample is classified as high-risk IPMN when the expression of the one or more mRNA and miRNA of Tables 1 and 2 are increased or decreased (e.g., by at least 2-fold or higher) compared to the expression level of the same biomarkers in the control sample. Further, the sample is classified as low-risk IPMN when the expression of the one or more mRNA and miRNA of Tables 1 and 2 is comparably similar to the expression level of the same biomarkers in the control sample. In some embodiments, the method of the present invention will also include a positive and/or negative control to assess the accuracy of the method.

Alternatively, after normalized biomarker expression levels are obtained, they are compared to predetermined expression cutpoints. In certain embodiments, the cutpoints define the numerical boundaries between (a) normalized expression levels that are high-risk IPMN and equivocal expression levels (i.e., the "upper" cutpoint) and (b) normalized expression levels that are low-risk IPMN and equivocal expression levels (i.e., the "lower" cutpoint). If a normalized biomarker expression level is not equivocal, the normalized biomarker expression level can be unequivocally designated as either a high-risk IPMN or low-risk IPMN expression level. Thus, the sample from which the normalized biomarker expression level was obtained can be designated as a high-risk IPMN or low-risk IPMN sample if it is not equivocal.

As noted above, the cutpoints are statistically validated in that they have been "trained" on prior samples that are known (via other, "validated" methods) to be either high-risk IPMN or low-risk IPMN. Alternatively, defined cutpoints for assays can be based on qRT-PCR or other test assays using a variety of statistical tests that are known in the art. Such statistical tests may include, but are not limited to: Pearson's Correlation, T-test, Mann-Whitney U test, binomial test, Wilcoxon signed-rank test, analysis of variance, as well as many others.

Once the cutpoints are determined using training samples, it is important that a test sample is assayed using the same assay parameters (e.g., the same primers, amplification conditions, normalization controls, data processing methods, etc.) as the training samples so that the results obtained using the test sample can be directly compared to the cutpoints to determine the status of the test sample.

The method of this invention is of use in predicting transition from pre-malignant cysts to malignancy thereby providing clinicians with the necessary information to treat patients with IPMN. For example, patients with low-risk lesions may have no need for surgery and will therefore be spared the physical, emotional and financial costs of a pancreatectomy. By comparison, a clinician may advise a patient with high-risk lesions to undergo surgery before the development of pancreatic cancer. Thus, this invention also provides the additional step of prophylactically or therapeutically treating a subject identified as having high-risk IPMN for pancreatic cancer to prevent, delay, ameliorate, slow or reverse the development or progression of pancreatic cancer. Prevention or treatment involves administering a pharmaceutically effective amount of a pancreatic cancer therapeutic or administering one or more other therapies (for example, radiotherapy, chemotherapy, immunotherapy, another type of anti-cancer agent, surgery, or a combination of two or more of the foregoing), directed at treating and/or preventing pancreatic cancer. As used herein, the term "preventing" encompasses avoiding development of the cancer, as well as delaying the onset of the cancer. In certain embodiments a combination of two or more therapies directed at treating pancreatic cancer are administered to the subject. In certain embodiments, the subject is treated with a kinase inhibitor.

In addition, the method of the invention can include determining biomarker expression at various times after administration of a drug or a therapy. A biomarker level detected in a biological sample from a subject at a first time (e.g., before giving the drug or therapy) that is higher than the biomarker level detected in a comparable biological sample from the same subject taken at a second time (e.g., after giving the drug or therapy), indicates that the pancreatic cancer in the subject is regressing.

In conjunction with the diagnostic and treatment method of the present invention, a kit for measuring the expression of one or more biomarkers disclosed herein is also provided. A kit of the invention includes a container containing suitable oligonucleotides or probes for hybridization or primer sets for amplifying nucleic acids encoding one or more of the biomarker mRNA of Table 1 and one or more of the biomarker miRNA of Table 2. In one embodiment, the kit includes the oligonucleotides or primers provided in Tables 4 and 5. In some embodiments, the kit can further include one or more binding agents that bind to the biomarker proteins listed in Table 3. Ideally, the at least includes probes or primers for measuring the expression of at least three of the following markers: IL1B, KRAS, PTGER2, PTGES2, hsa-miR-101, hsa-miR-18a, hsa-miR-217, and hsa-miR-342-3p. In yet other embodiments, the kit can include a set of primers for amplifying a reference mRNA. In certain embodiments, the reference mRNA is RPLP0. Exemplary primers of use in amplifying RPLP0 mRNA are: forward primer, 5'-TGGTCATCCAGCAGGTGTTCGA-3' (SEQ ID NO:58) and reverse primer 5'-ACAGACACTGGCAACATTGCGG-3' (SEQ ID NO:59).

The kit can also contain other solutions and controls, necessary or convenient for carrying out the invention. The container can be made of glass, plastic or foil and can be a vial, bottle, pouch, tube, bag, etc. The kit may also contain written information, such as procedures for carrying out the present invention or analytical information, such as the amount of reagent contained in the first container means, as well as the software for the analysis and presentation of results. The container can be in another container, e.g., a box or a bag, along with the written information.

In one embodiment, the kit includes a solid support, such as a chip, a microtiter plate or a bead or resin having a capture reagent (e.g., an antibody or oligonucleotide) attached thereon, wherein the capture reagent binds a biomarker of the invention or nucleic acid encoding the same. The kit can also include a washing solution or instructions for making a washing solution, in which the combination of the capture reagent and the washing solution allows capture of the biomarker or biomarker nucleic acids on the solid support for subsequent detection. The kit may include more than one type of adsorbent, each present on a different solid support.

In some embodiments, the current invention provides a kit for performing a barcode-based (e.g., NanoString™ based) assay to quantify expression of mRNAs and miRNAs belonging to a profile of differentially expressed molecules in a sample of an individual having pancreatic cancer. NanoString™ based assays are described in U.S. Pat. Nos. 8,415,102, 8,519,115, and 7,919,237.

Using the kit and method of the invention, the relative gene expression values may be normalized and transformed, then evaluated in a predictive model to characterize a patient's pancreatic IPMN cyst as having a high risk of malignancy (high-grade dysplasia or invasive cancer) or low risk of malignancy (low or moderate grade of dysplasia). The model may be based on an algorithm where the expression of each gene is weighted based on its ability to predict the outcome. Genes that do not contribute to the outcome may be removed in order to decrease or minimize variables in the algorithm thereby reducing the complexity and bias of the model.

As an example, the number of biomarkers in a predictive algorithm may include six biomarkers, e.g., miR21, miR342, IL1B, KRAS, MUC4, and PTGES2. Using the formula: y=0.44+(−0.11 miR217)+(0.03 miR342)+(−0.08 IL1B)+(0.23 KRAS)+(−0.25 MUC4)+(−0.85 PTGES2), the model has an AUC of 0.82 (p=0.003) to differentiate low from high-risk cysts.

As another example, where there is a mutation in both Gnas and Kras, the number of biomarkers in a predictive algorithm may include eight biomarkers, e.g., miR342, IL1B, KRAS, MUC4, MUC7, PTGER2, PTGES2 and TP63. Using the formula: y=0.49+(0.17 miR342)+(−0.17 IL1B)+(0.18 KRAS)+(−0.27 MUC4)+(0.02 MUC7)+(0.07 PTGER2)+(−0.95 PTGES2)+(0.02 TP63), the model has an AUC of 0.82 (p=0.003).

As a further example, where there is a mutation in either Gnas or KRAS, the number of biomarkers in a predictive algorithm may include three biomarkers, IL1B, MUC4 and PTGES2. Using the formula: y=0.37+(−0.06 IL1B)+(−0.01 MUC4)+(−0.50 PTGES2), the model has an AUC of 0.86 (p=0.002) to predict that an IPMN will be high risk.

As yet a further example, where there is more than one mutation in either Gnas or Kras, the number of biomarkers in a predictive algorithm may include nine biomarkers, miR142, miR342, IL1B, KRAS, MUC4, MUC7, PTGER, TP63 and PTGES2. Using the formula: y=0.51+(0.01 miR142)+(0.21 miR342)+(−0.18 IL1B)+(0.20 KRAS)+(−0.37 MUC4)+(0.09 MUC7)+(0.16 PTGER2)+(−1.09 PTGES2)+(0.07 TP63), the model has an AUC of AUC=0.86 (p=0.002) to predict that an IPMN will be high risk.

In a particular embodiment, the number of biomarkers in a predictive algorithm includes only three genes, i.e., IL1B, MUC4 and PTGES2. Using the formula: y=0.37+(−0.06 IL1B)+(−0.01 MUC4)+(−0.50 PTGES2), the model has an AUC of 0.86 (p=0.002) to predict that an IPMN will be high risk when y is greater than 0.5.

Accordingly, in certain embodiments, the biomarkers used in the method and kit of this invention include hsa-miR-21, hsa-miR-142-3p, hsa-miR-342-3p, IL1B, KRAS, MUC4, MUC7, PTGER, TP63 and PTGES2. In other embodiments, the biomarkers used in the method and kit of this invention include IL1B, MUC4, and PTGES2. In yet other embodiments, the biomarkers used in the method and kit of this invention consist of IL1B, MUC4, and PTGES2. In further embodiments, the biomarkers used in the method and kit of this invention comprise, at the very least, IL1B, MUC4, and PTGES2 and may include the one or more of the markers in Tables 1-3.

This invention also pertains to a method of screening compounds for use in the treatment of pancreatic cancer by providing a sample of pancreatic IPMN cyst fluid; and one or more test compounds; and contacting the pancreatic IPMN cyst fluid sample with the test compound; and detecting a change in the expression of one or more biomarker miRNA, mRNA or proteins disclosed herein in the pancreatic cell sample in the presence of the test compound relative to the absence of the test compound. In some embodiments, the cell is in vitro or in vivo. In other embodiments, candidate compounds are antisense agents (e.g., antisense or RNAi molecules) directed against a biomarker miRNA or mRNA of the present invention. In other embodiments, candidate compounds are antibodies that specifically bind to a biomarker protein of the present invention.

Specifically, the present invention provides screening methods for identifying modulators, i.e., candidate or test compounds or agents (e.g., proteins, peptides, peptidomimetics, peptoids, small molecules or other drugs) that bind to biomarkers of the present invention, have an inhibitory (or stimulatory) effect on, for example, biomarker expression or biomarker activity, or have a stimulatory or inhibitory effect on, for example, the expression or activity of a biomarker substrate.

Compounds thus identified can be used to modulate the activity of target gene products (e.g., biomarker genes) either directly or indirectly in a therapeutic protocol, to elaborate the biological function of the target gene product, or to identify compounds that disrupt normal target gene interactions. Compounds that inhibit the activity or expression of biomarkers are useful in the treatment of proliferative disorders, e.g., cancer.

The test compounds of the present invention can be obtained using any of the numerous approaches in combinatorial library methods known in the art, including biological libraries; peptoid libraries (libraries of molecules having the functionalities of peptides, but with a novel, non-peptide backbone, which are resistant to enzymatic degradation but which nevertheless remain bioactive; spatially addressable parallel solid phase or solution phase libraries; synthetic library methods requiring deconvolution; the 'one-bead one-compound' library method; and synthetic library methods using affinity chromatography selection. The biological library and peptoid library approaches are preferred for use with peptide libraries, while the other four approaches are applicable to peptide, non-peptide oligomer or small molecule libraries of compounds.

In one embodiment, an assay is a cell-based assay in which a cell that expresses a biomarker protein or biologically active portion thereof is contacted with a test compound, and the ability of the test compound to the modulate biomarker activity is determined. Determining the ability of the test compound to modulate biomarker activity can be accomplished by monitoring, for example, changes in enzymatic activity. The cell, for example, can be of mammalian origin.

In yet another embodiment, a cell-free assay is provided in which a biomarker protein or biologically active portion thereof is contacted with a test compound and the ability of the test compound to bind to the biomarker protein or biologically active portion thereof is evaluated. Preferred biologically active portions of the biomarkers proteins to be used in assays of the present invention include fragments that participate in interactions with substrates or other proteins, e.g., fragments with high surface probability scores.

Cell-free assays involve preparing a reaction mixture of the target gene protein and the test compound under conditions and for a time sufficient to allow the two components to interact and bind, thus forming a complex that can be removed and/or detected. The interaction between two molecules can also be detected, e.g., using fluorescence energy transfer (FRET). Alternatively, the ability of the biomarkers protein to bind to a test compound can be accomplished using real-time Biomolecular Interaction Analysis (BIA).

Modulators of biomarker expression can also be identified. For example, a cell or cell free mixture is contacted with a candidate compound and the expression of biomarker mRNA or protein is evaluated relative to the level of expression of the biomarker mRNA or protein in the absence of the candidate compound. When expression of the biomarker mRNA or protein is greater in the presence of the candidate compound than in its absence, the candidate compound is identified as a stimulator of biomarker mRNA or protein expression. Alternatively, when expression of biomarker mRNA or protein is less (i.e., statistically significantly less) in the presence of the candidate compound than in its absence, the candidate compound is identified as an inhibitor of biomarker mRNA or protein expression. The level of biomarker mRNA or protein expression can be determined by methods described herein for detecting biomarker mRNA or protein.

The following non-limiting examples are provided to further illustrate the present invention.

EXAMPLE 1

Single-Platform Cyst Fluid Assay to Accurately Predict IPMN with High-Malignant Potential for Surgical Resection Biological Samples. The international IPMN cyst fluid collaborative is composed of groups from high-volume pancreatic surgery centers with an expertise in IPMN across Europe and the United States that was born out of the Verona Consensus Conference (Adsay, et al. (2016) *Ann. Surg.* 263(1):162-77; Maker, et al. (2015) *J. Am. Coll. Surg.* 220(2):243-53). IPMN cyst fluid samples were obtained from prospectively maintained institutional databases/repositories after Institutional Review Board approval. Only samples with a confirmed diagnosis of IPMN on final pathology and with the specific grade of dysplasia determined by an expert pancreatic pathologist were included in the study. The highest grade of dysplasia found in the cyst determined its characterization as low-grade, moderate-grade, high-grade or invasive cancer. Analysis evaluated samples by specific grade individually, e.g., low, medium, high, invasive; and by "low-risk" (low and moderate-grade dysplasia) or "high-risk" (high-grade dysplasia and invasive cancer) pathology for the purpose of risk-stratification, as has been used in multiple other biomarker studies in this field (Maker, et al. (2011) *Ann. Surg. Oncol.* 18(1):199-206; Maker, et al. (2011) *Clin. Cancer Res.* 17(6):1502-8).

Quantitative Analysis of mRNAs and miRNAs. Total RNA was extracted from 100-400 µl of IPMN fluids using Quick-RNA™ MicroPrep R1050/R1051 (Irvine, Calif.), implemented on a Maxwell® 16 instrument for automated nucleic acid extraction. DNAse treatment was performed on the instrument according to the manufacturer's instructions. Subsequently, the total RNA was split into two paths for mRNA and miRNA analysis using quantitative PCR.

For analysis of mRNA, total RNA was reverse transcribed using random primers and the High Capacity cDNA reverse transcription kit (Thermo Fisher Scientific), according to the manufacturer's instructions. cDNA was prepared for quantitative PCR (qPCR) using a pre-amplification step, with the Taqman® PreAmp master mix kit (Thermo Fisher Scientific). Taqman® gene expression assays were pooled to serve as primers for the pre-amplification step according to the manufacturer's instructions. Assays included IL1B (Hs01555410_m1), MUC-1 (Hs00159357_m1), MUC-2 (Hs00894025_m1), MUC-4 (Hs00366414_m1), MUC-5ac (Hs01365616_m1), MUC-7 (Hs00379529_m1), PTGER2 (Hs04183523_m1), PTGS1 (Hs00377726 m1), PGE2-R (Hs00168755_m1), KRAS (Hs00364282_m1), GNAS (Hs00255603_m1), GADPH (Hs99999905_m1), RPLP0 (Hs99999902_m1), TP63 (Hs00978341_m1), ERBB2 (Hs01001580_m1), PTGES2 (Hs00228159_m1). Pre-amplified cDNA was then used as template for qPCR reactions with individual assays. Reactions were performed using Taqman® Fast Advanced Mastermix (Thermo Fisher Scientific) in 384-well plates using a ViiA7 real-time PCR instrument (Life Technologies). All reactions were performed in triplicate, and in volumes of 10 µl. Real-time data were processed using the comparative C(t) method (Schmittgen & Livak (2008) *Nature Protocols* 3(6):1101-8). The chosen endogenous control gene was RPLP0, based on performance across the entire dataset.

Analysis of miRNAs was performed in a similar fashion to mRNAs. Reverse transcription was performed using the Taqman® microRNA reverse transcription kit (Thermo Fisher Scientific), with Taqman® miRNA assays in place of random primers. The assays used for this study included miR17-3p (hsa-miR-17-3p), miR142-3p (hsa-miR-142-3p), miR532-3p (hsa-miR-532-3p), miR342-3p (hsa-miR-342-3p), miR30a-3p (hsa-miR-30a-3p), miR21 (hsa-miR-21-5p), miR155 (hsa-miR-155-5p), mir101 (hsa-miR-101-3p), mir10a (hsa-miR-10a-5p), miR106b (hsa-miR-106b-5p), miR18a (hsa-miR-18a-5p), miR217 (hsa-miR-217), miR24 (hsa-miR-24-3p), miR92a (hsa-miR-92a-3p), miR99b (hsa-miR-99b-5p), and the gene RNU6B. miRNA qPCR was performed as described above for mRNA assays, using the individual Taqman® miRNA assays. Real-time data were processed using the comparative C(t) method, using the RPLP0 gene as an endogenous control.

PCR Amplification and Sanger Sequencing of GNAS and KRAS Mutation Sites. Genomic DNA was extracted from 100-400 µl of IPMN fluids using the Maxwell® 16 Tissue DNA kit (Promega, Madison, Wis.) on a Maxwell® 16 instrument. Mutation analysis of codons 12 and 13 in KRAS and codon 201 in GNAS were performed by PCR followed by Sanger sequencing. Each 50 µl PCR reaction contained 1× PCR buffer with 1.5 mM MgCl$_2$, 0.5 µl HotStarTaq® DNA polymerase (Qiagen, Germantown, Md.), 0.2 mM dNTP mix (Sigma-Aldrich Corp., St Louis, Mo.), 20 pmols of forward and reverse primers and 5 µl DNA template.

Primer sequences were as follows: KRAS-F 5f-TGGTG-GAGTATTTGATAGTGTATTAACCTTAT-3' (SEQ ID NO:60), KRAS-R 5'-AAACAAGATTTACCTCTAT-TGTTGGATCATA-3' (SEQ ID NO:61), GNAS-F 5'-TCT-GAGCCCTCTTTCCAAACTAC-3' (SEQ ID NO:62), GNAS-R 5'-GGACTGGGGTGAATGTCAAGAA-3' (SEQ ID NO:63) (Integrated DNA Technologies, Coralville, Iowa). The KRAS PCR reaction in addition contained 25 pmols of an LNA oligo to suppress wild-type amplification (Exiqon, Woburn, Mass.). After an initial denaturation step at 95° C. for 15 minutes, 40 cycles of PCR were performed as follows: 95° C. for 30 seconds, 52° C. for 30 seconds, 68° C. for 30 seconds with a final elongation step at 68° C. for 10 minutes. Amplification products were purified and bi-directionally sequenced on an ABI3130XL genetic analyzer using the PCR primers and the BigDye® 3.1 terminator cycle sequencing kit. Sequence chromatograms were visualized manually to determine if a mutation was present. The analytical sensitivity is 1% mutant sequence for KRAS codons 12 and 13 and 15% mutant sequence for GNAS codon 201. Appropriate positive and contamination controls were included. Mutation nomenclature was according to standard guidelines.

Statistical Analysis. Cyst fluid gene expression levels were processed to obtain RQ values that were z-transformed, log2 transformed, and scaled (X-mean/standard deviation). Pearson correlation coefficients were utilized to remove highly correlated variables with a cutoff of 0.7. Principle coordinate analysis was then performed. Models were run adding sequencing data from Kras and Gnas mutational analysis and evaluated as +kras mutation, +gnas mutation, +gnas/+kras mutation, or 0, 1, or 2 mutations. Mutational analysis as an independent variable was appended to the data matrix with 22 markers for learning and utilized in classification and regression analysis by a support vector machine (SVM) training algorithm. Individual markers were assessed for associations with level of dysplasia. R package glmnet was used together with logistic regression for classification of the samples. Batch effect correction was performed. Highly-corrected markers were removed. Lasso-penalized logistic regression with binary classification and 5-fold cross validation utilized AUC as evaluation criteria to create the optimal signature.

Selection of Targets and Cyst Fluid. The instant study involved 14 mRNA markers, 15 miRNA targets, and GNAS codon 201 and KRAS codons 12 and 13 point mutational analysis. A multi-institutional international IPMN cyst fluid collaborative was developed to contribute patient samples for this study. A total of 134 cyst fluid samples were evaluated for inclusion. Sufficient fluid volume of samples with specific IPMN pathology and grade of dysplasia (low, moderate, high-grade, invasive) was confirmed for 59 cyst fluid samples. 95% of samples contained sufficient genomic material for further analysis.

Principal Component Analysis, Batch Effect Correction, Removal of Confounders. Principal component analysis demonstrated minimal institutional bias/clustering which was batch effect corrected. As highly corrected biomarkers will cause difficulties in machine learning algorithms to identify individual features for the signature, a Pearson correlation matrix was calculated between each pair of markers. Within each group of highly correlated markers (Pearson correlation >0.7), one representative marker was kept for further analysis using R package caret. Thus, confounding markers (i.e., miR-106B, miR-155, miR-24, miR-532, miR-92A and GNAS) were removed from the analysis.

Specific Mutational Analysis. GNAS codon 201 and KRAS codons 12 and 13 were sequenced for mutational analysis. Of 49 samples with sufficient DNA harvested from the cyst fluid to reliably sequence, 30 contained a point mutation in GNAS or KRAS. For GNAS, seven samples had p.R201H mutations and six had p.R201C mutations; while for KRAS, seven had a p.G12R mutation, 14 had a p.G12V mutation, eight had a p.G12D mutation, 1 had a G12F mutation, 1 had a p.G12A mutation and one had a p.G13D mutation. Three samples each had two KRAS codon 12 point mutations. Nine samples contained both GNAS codon 201 and KRAS codon 12 mutations, of which 1 also contained the KRAS codon 13 mutation.

Lasso Regression Results. After removing highly correlated markers, a machine learning algorithm was employed to perform feature selection which identified the markers significantly related to the level of dysplasia/risk of pancreatic malignancy. Lasso (Least absolute shrinkage and selection operator) regression analysis performed both variable selection and regularization that improved the prediction accuracy and interpretability of the regression model by altering the model fitting process to select only a subset of the IPMN grade predictive covariates for use in the final model. In N patient cyst fluids, each of which was composed of p predictive genes and a level of dysplasia as single outcome; $y_i$ is the classification of dysplasia and $x_i=(x_1, x_2, \ldots, x_v)^T$ the gene expression (covariate vector) for the $i^{th}$ case. This resulted in the objective of lasso to solve $$\min_{\beta \in R^p} \left\{ \frac{1}{N} \|y - X\beta\|_2^2 + \lambda \|\beta\|_1 \right\}$$

where the aim is to identify the least number but optimal subset of markers which minimize the classification error between high and low-risk IPMN (Lockhart, et al. (2014) *Ann. Statist.* 42(2):413-68; Friedman, et al. (2010) *J. Statist. Soft.* 33(1):1-22).

In a binomial logistic regression model with area under the curve (AUC) as the objective function, the maximum AUC was achieved with miR21, miR342, IL1B, KRAS, MUC4, and PTGES2 resulting in an AUC of 0.82 (p=0.003) to differentiate low-risk from high-risk cysts. Subset analysis including iterations involving Gnas and Kras point mutation analysis were performed to determine the most accurate predictive biosignature. When a mutation in either Gnas or Kras was considered, the most predictive signature was achieved with IL1B, MUC4, and PTGES2 to construct the accurate equation of: y=0.37+(−0.06 IL1B)+(−0.01 MUC4)+(−0.50 PTGES2), AUC=0.86, p-value=0.002 (FIG. 1).

Evidence supports a progression model for IPMN from low grade dysplasia to adenocarcinoma, however, the time frame for this transformation is unknown. Some lesions will progress to cancer, while others may remain as low-risk lesions for decades. Though ideally the risk of malignancy would be determined preoperatively, currently many cysts at low-risk of malignant transformation are being removed at the expense of mental, physical, and financial cost for patients, with the added risk of ~2% mortality and ~40% morbidity post-operatively. This risk to benefit ratio is the crux of the challenge in surgical decision making for this disease, where the ramifications of missing an occult pancreatic adenocarcinoma, or delay in resection that allows progression to malignancy, may result in significant cancer-related mortality. For this reason, some groups advocate even resection of known low-risk lesions. In the United States, the vast majority of patients currently undergoing surgical resection for IPMN will have low-risk cysts determined on final pathology despite multiple U.S., European, and international guidelines to direct patient selection towards high-risk lesions. It has been demonstrated that up to 65% of lesions predicted by the guidelines to be high-risk for high-grade dysplasia or invasive cancer are found to be low-risk on final pathology, while other small BD-IPMN predicted to have a low-risk of malignancy with the same guidelines will demonstrate high-risk pathology up to 25% of the time.

The two most commonly used guidelines for clinical decision making in the United States are the revised Sendai (Fukuoka) and American Gastroenterological Association (AGA) guidelines. Fukuoka has been found to have a high false positive rate with 21% specificity for malignancy. The same study found AGA guidelines to have a lower false positive rate with 44% specificity, but with a higher false-negative rate and 12% more of malignancies overlooked. Similar analysis of the current guidelines supported that Fukuoka had a 65-72% false negative rate to identify high-risk cysts while AGA misidentified 45% of high-risk IPMN. Thus, the field is need of novel and reliable biomarkers that will be able to differentiate between cysts with minimal risk of malignant transformation and those with high-risk pathology or occult malignancy.

In response to this need, an IPMN cyst fluid gene biosignature has now been developed with the ability to discriminate high-risk with up to 86% accuracy. All high-risk cysts should be surgically excised in otherwise fit and medically-appropriate individuals, and low-risk cysts can at a minimum be characterized with this quantitative data that can be used for informed surgical decision making and informed consent.

Bias in this study was minimized as much as possible by including an international multi-institutional cohort, a large number of patient cyst fluid samples, running samples in large batches, preselecting candidate biomarkers, and through robust statistical methods with 5-fold cross-validation. Interestingly, when kras and gnas mutational analysis were added to the model, they were not selected as contributing features to the predictive value, possibly because of the high prevalence of these mutations in IPMN overall.

---

What is claimed is:

1. A kit for differentiating between high-risk and low-risk intraductal papillary mucinous neoplasms and the level of cyst dysplasia, comprising primer sets for amplifying biomarker RNAs,
wherein the primer sets are barcoded.

2. The kit of claim 1, wherein the kit further comprises one or more binding agents that bind biomarker proteins selected from the group of ERRB2, GAPDH, GNAS, IL1B, KRAS, MUC-1, MUC-2, MUC-4, MUC-5AC, MUC-7, PGE2-R and PTGER2.

3. The kit of claim 1, further comprising a primer set for amplifying a reference mRNA.

4. The kit of claim 3, wherein the reference mRNA is RPLP0.

5. A kit for differentiating between high-risk and low-risk intraductal papillary mucinous neoplasms and the level of cyst dysplasia, comprising primer sets for amplifying biomarker RNAs MUC-4, hsa-miR-342-3p, IL1B, and PTGES2,
wherein the primer sets are barcoded.

6. The kit of claim 5, wherein the kit further comprises one or more binding agents that bind biomarker proteins selected from the group of ERRB2, GAPDH, GNAS, IL1B, KRAS, MUC-1, MUC-2, MUC-4, MUC-SAC, MUC-7, PGE2-R and PTCER2.

7. The kit of claim 5, further comprising a primer set for amplifying a reference mRNA.

8. The kit of claim 7, wherein the reference mRNA is RPLP0.

9. A kit for differentiating between high-risk and low-risk intraductal papillary mucinous neoplasms and the level of cyst dysplasia, comprising primer sets for amplifying biomarker messenger RNAs IL1B, MUC-4, and PTGES2,
wherein the primer sets are barcoded.

10. The kit of claim 9, wherein the kit further comprises one or more binding agents that bind biomarker proteins selected from the group of ERRB2, GAPDH, GNAS, IL1B, KRAS, MUC-1, MUC-2, MUC-4, MUC-5AC, MUC-7, PGE2-R and PTGER2.

11. The kit of claim 9, further comprising a primer set for amplifying a reference mRNA.

12. The kit of claim 11, wherein the reference mRNA is RPLP0.

* * * * *